(12) United States Patent
Kaku et al.

(10) Patent No.: US 9,022,650 B2
(45) Date of Patent: May 5, 2015

(54) X-RAY IMAGING APPARATUS

(71) Applicant: Canon Kabushiki Kaisha, Tokyo (JP)

(72) Inventors: Wataru Kaku, Yokohama (JP);
Yoshihiro Miyazawa, Tokyo (JP);
Hideki Hayashi, Kiyose (JP); Takashi Ogura, Tokyo (JP); Jun Murata, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 293 days.

(21) Appl. No.: 13/729,418

(22) Filed: Dec. 28, 2012

(65) Prior Publication Data

US 2013/0188781 A1 Jul. 25, 2013

(30) Foreign Application Priority Data

Jan. 19, 2012 (JP) .................. 2012-009430

(51) Int. Cl.
  *H05G 1/02* (2006.01)
  *G01N 23/20* (2006.01)
  *A61B 6/06* (2006.01)
  (Continued)

(52) U.S. Cl.
  CPC . *H05G 1/02* (2013.01); *A61B 6/107* (2013.01); *A61B 6/4405* (2013.01); *A61B 6/4429* (2013.01)

(58) Field of Classification Search
  CPC .... A61B 6/4405; A61B 6/548; A61B 6/4429; A61B 6/547; A61B 6/4494; A61B 6/06; A61B 6/4283; A61B 6/4291; A61B 6/447; A61B 6/508; A61B 6/56; A61B 6/0002; A61B 6/0059; A61B 6/0091; A61B 6/4312; A61B 6/4528; A61B 6/025; A61B 6/102; A61B 6/4021; A61B 6/4417; A61B 6/4423; A61B 6/4441; A61B 6/4452; A61B 6/502; A61B 6/5247; A61B 6/54; A61B 6/563; A61B 6/588; A61B 8/00; A61B 8/0825; A61B 8/4416; A61B 8/4472; G01N 23/04; G01N 23/043; G01N 23/20; G01N 23/201; G01N 23/203
  USPC ........... 378/198, 197, 196, 102, 62, 146, 193, 378/117
  See application file for complete search history.

(56) References Cited

U.S. PATENT DOCUMENTS 2,764,694 A * 9/1956 Kinzer .......................... 378/190
5,138,646 A * 8/1992 Hubert et al. ................. 378/177
5,784,435 A * 7/1998 Figurski ....................... 378/197

(Continued)

FOREIGN PATENT DOCUMENTS

JP  11-104117  4/1999
JP  2011-56170  3/2011

*Primary Examiner* — David A Vanore
(74) *Attorney, Agent, or Firm* — Fitzpatrick, Cella, Harper & Scinto

(57) ABSTRACT

An X-ray imaging apparatus comprises an X-ray generation unit; a plurality of supporting members configured to support the X-ray generation unit; and an accommodation unit configured to accommodate the X-ray generation unit and the plurality of supporting members, wherein the accommodation unit is formed by bringing a first member and a second member into contact with each other, each of the plurality of supporting members is connected to the first member by a first connecting portion that is rotatable and to the X-ray generation unit by a second connecting portion that is rotatable, and a support height of the X-ray generation unit supported by the supporting members can be adjusted in accordance with a distance between the first member and the second member.

15 Claims, 6 Drawing Sheets

(51) Int. Cl.
 *A61B 6/00* (2006.01)
 *A61B 6/10* (2006.01)

(56) References Cited

U.S. PATENT DOCUMENTS

| | | | |
|---|---|---|---|
| 7,322,745 B2* | 1/2008 | Agrawal et al. | 378/198 |
| 7,664,222 B2* | 2/2010 | Jabri et al. | 378/26 |
| 7,748,900 B2* | 7/2010 | Maschke | 378/198 |
| 7,796,734 B2* | 9/2010 | Mastronardi et al. | 378/90 |
| 7,810,994 B2* | 10/2010 | Ohmura et al. | 378/196 |
| 8,031,838 B2* | 10/2011 | Bowers et al. | 378/117 |
| 8,194,822 B2* | 6/2012 | Rothschild et al. | 378/88 |
| 8,568,028 B2* | 10/2013 | Wendlandt et al. | 378/198 |
| 8,576,982 B2* | 11/2013 | Gray et al. | 378/57 |
| 8,721,176 B2* | 5/2014 | McBroom et al. | 378/189 |
| 8,734,013 B2* | 5/2014 | Singh | 378/197 |
| 8,891,734 B2* | 11/2014 | Lalena et al. | 378/116 |
| 2013/0177134 A1* | 7/2013 | Tay | 378/57 |
| 2013/0182828 A1* | 7/2013 | Watanabe et al. | 378/145 |
| 2013/0230142 A1* | 9/2013 | Murata et al. | 378/62 |
| 2014/0133627 A1* | 5/2014 | Sakuragi et al. | 378/62 |
| 2014/0177797 A1* | 6/2014 | Ogura et al. | 378/62 |
| 2014/0211916 A1* | 7/2014 | Morton | 378/57 |

* cited by examiner

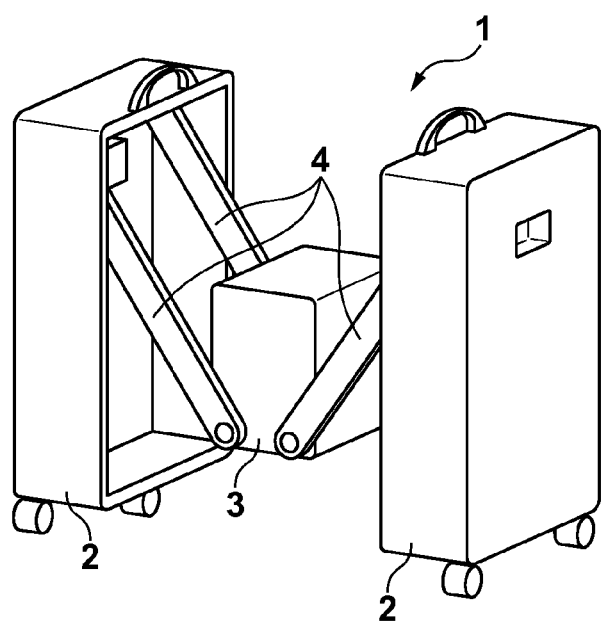
F I G. 2A
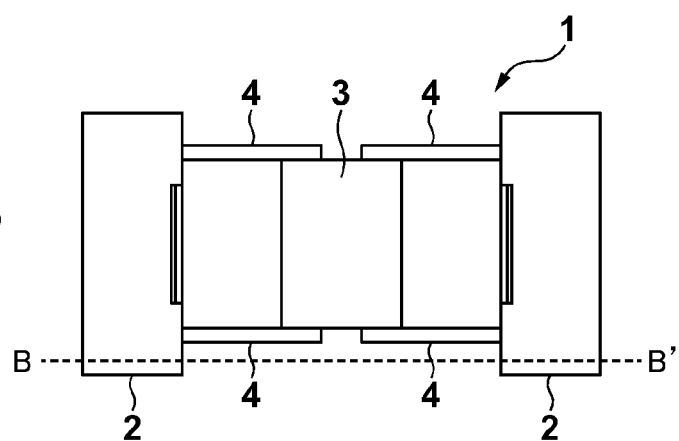
F I G. 2B
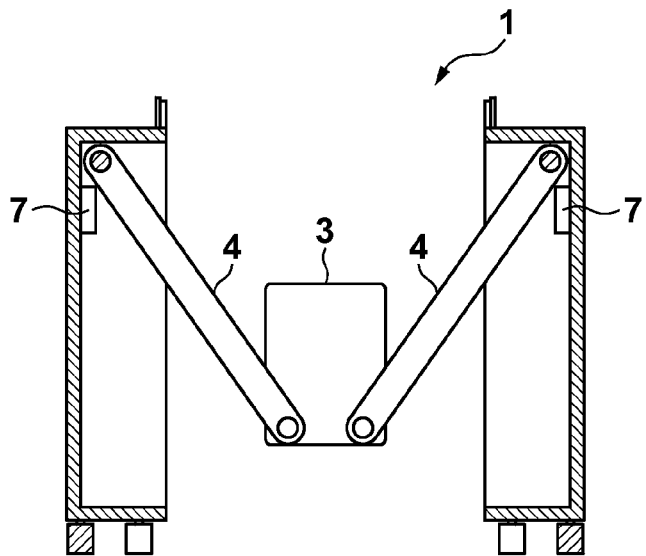
F I G. 2C

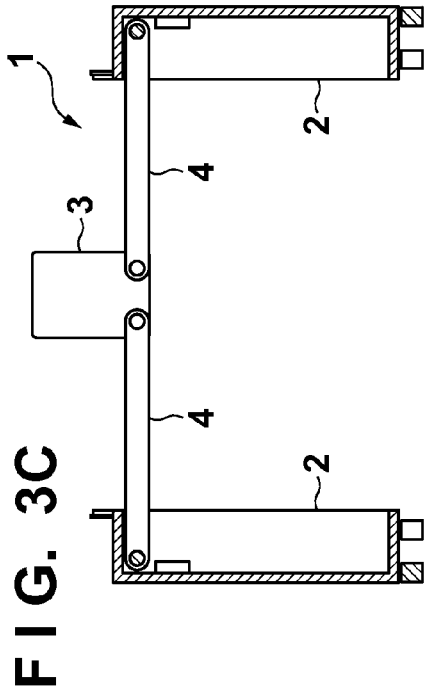
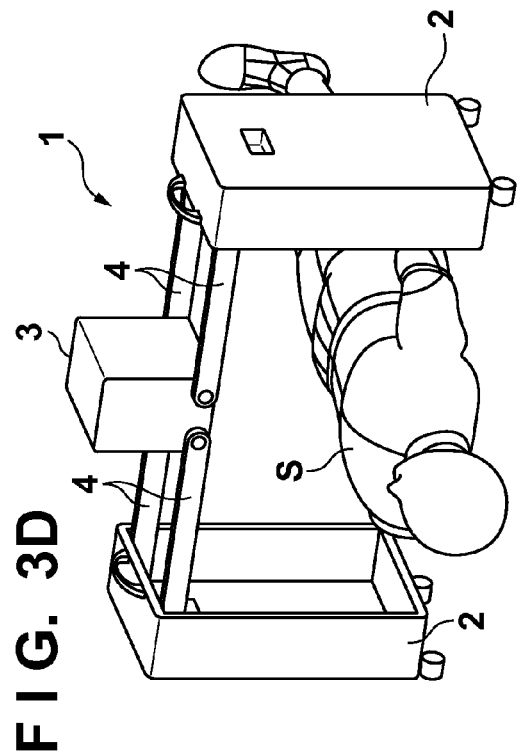
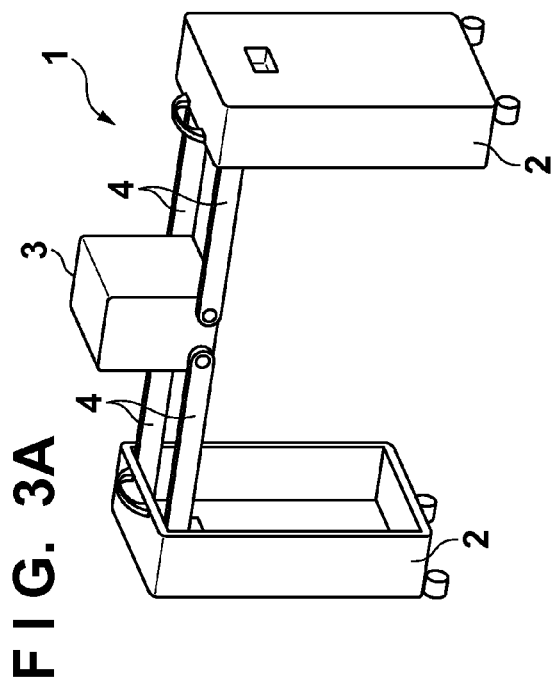
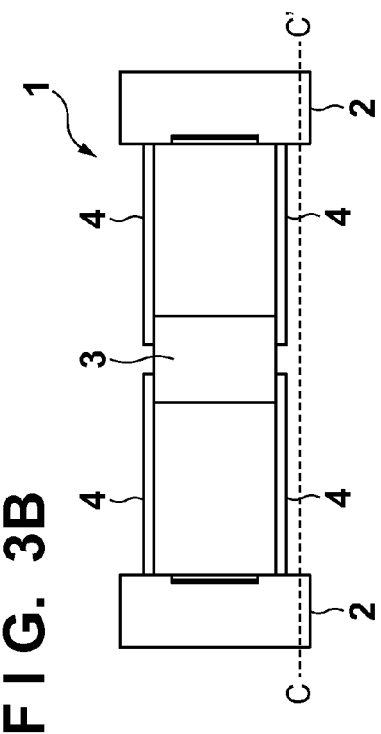
FIG. 3A  FIG. 3C
FIG. 3B  FIG. 3D

F I G. 5
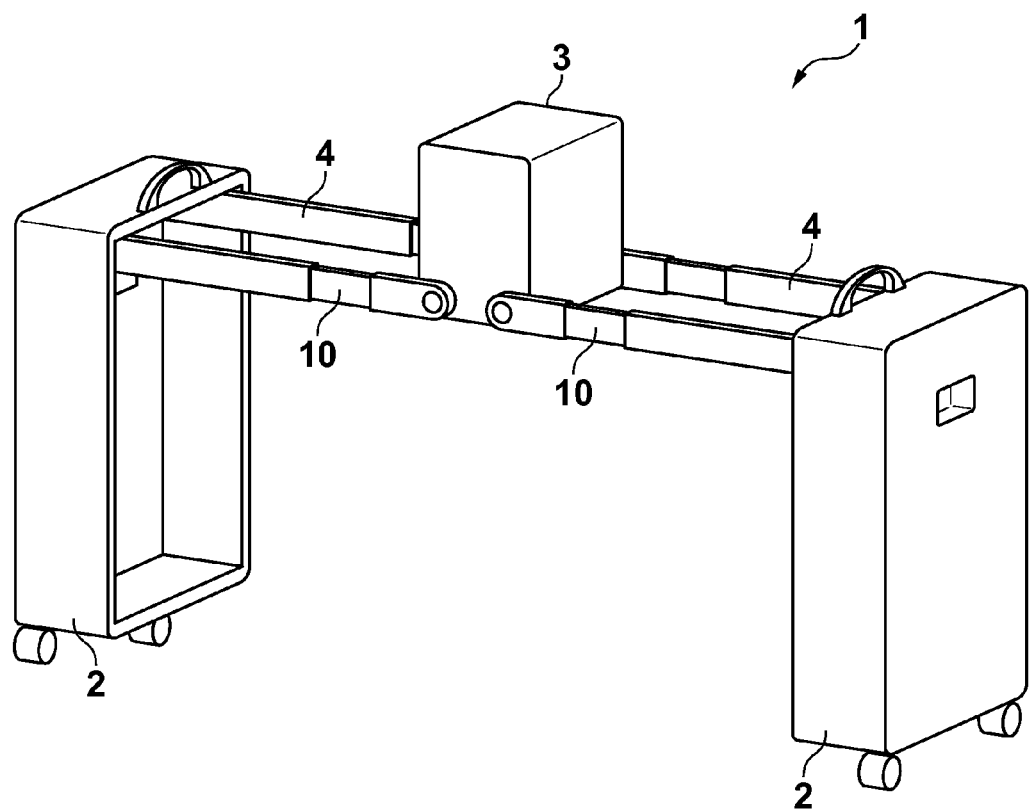

X-RAY IMAGING APPARATUS

BACKGROUND OF THE INVENTION

1. Field of the Invention

The present invention relates to an X-ray imaging apparatus.

2. Description of the Related Art

There have recently been proposed X-ray imaging apparatuses whose portability is increased by reducing the size and weight for X-ray imaging at home or at a site of disaster.

Japanese Patent Laid-Open No. 2011-56170 discloses an X-ray imaging apparatus that performs imaging using an X-ray generation unit hung from a collapsible frame so as to be located vertically above the imaging part.

Japanese Patent Laid-Open No. 11-104117 discloses a trunk-type X-ray imaging apparatus that allows the user to take out an X-ray generation unit, a frame, and an X-ray detection sensor accommodated in a truck-type case, assemble them, and perform imaging.

In the X-ray imaging apparatus disclosed in Japanese Patent Laid-Open No. 2011-56170, however, the operation of assembling the frame and hanging the X-ray generation unit at the time of installation is cumbersome and time-consuming. Upon transport as well, the operation of detaching the X-ray generation unit and collapsing the frame is cumbersome and time-consuming. In addition, the portability is poor because the collapsible frame and the X-ray generation unit are separate.

In the X-ray imaging apparatus disclosed in Japanese Patent Laid-Open No. 11-104117, the operation of taking out the parts from the case and assembling them at the time of installation is cumbersome and time-consuming. Upon transport as well, the operation of detaching the parts and accommodating them in predetermined places of the case is cumbersome and time-consuming.

In X-ray imaging at home or at a site of disaster, the imaging target subject often remains lying down due to injuries or illness. The operation for installing or collapsing the X-ray imaging apparatus disclosed in Japanese Patent Laid-Open No. 2011-56170 or 11-104117 need to be performed while keeping the subject lying down. If the user accidentally lets a part drop during the operation, the part may not only break but also hurt the subject. In addition, the place where the subject lies down at home or a site of disaster varies (the ground, the presence/absence of bedding such as a mattress or a bed, the width, the height, and the like are different), and the imaging condition is not constant in many cases. However, the X-ray imaging apparatuses disclosed in Japanese Patent Laid-Open Nos. 2011-56170 and 11-104117 cannot perform imaging in correspondence with various imaging conditions because they have a predetermined frame length.

SUMMARY OF THE INVENTION

In consideration of the above-described problems, the present invention provides an X-ray imaging apparatus that is convenient in transport and installation and can perform X-ray imaging in correspondence with various imaging conditions.

According to one aspect of the present invention, there is provided an X-ray imaging apparatus comprising: an X-ray generation unit; a plurality of supporting members configured to support the X-ray generation unit; and an accommodation unit configured to accommodate the X-ray generation unit and the plurality of supporting members, wherein the accommodation unit is formed by bringing a first member and a second member into contact with each other, each of the plurality of supporting members is connected to the first member by a first connecting portion that is rotatable and to the X-ray generation unit by a second connecting portion that is rotatable, and a support height of the X-ray generation unit supported by the supporting members can be adjusted in accordance with a distance between the first member and the second member.

Further features of the present invention will be apparent from the following description of exemplary embodiments with reference to the attached drawings.

BRIEF DESCRIPTION OF THE DRAWINGS

FIGS. 2A to 2C are views showing the schematic arrangement of the X-ray imaging apparatus according to the first embodiment at the time of transformation;

FIGS. 3A to 3D are views showing the schematic arrangement of the X-ray imaging apparatus according to the first embodiment at the time of imaging;

FIG. 5 is a perspective view showing the schematic arrangement of the X-ray imaging apparatus according to the second embodiment.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1A:
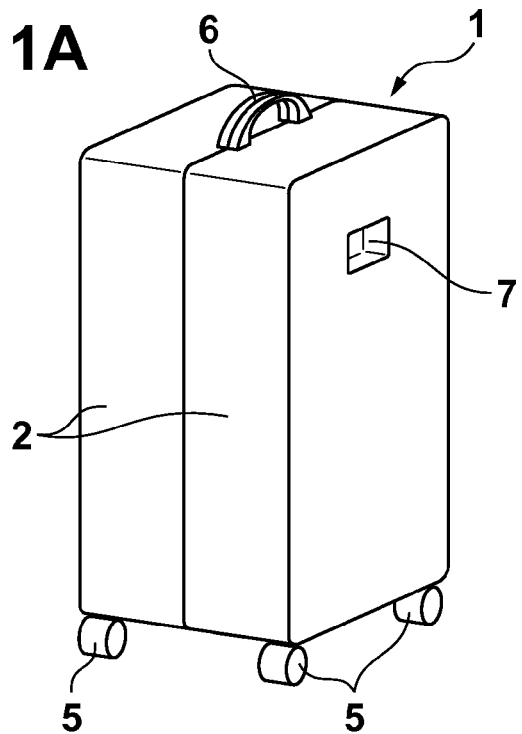
FIGS. 1A to 1C are views showing the schematic arrangement of an X-ray imaging apparatus according to the first embodiment at the time of accommodation.
Figure 1B:
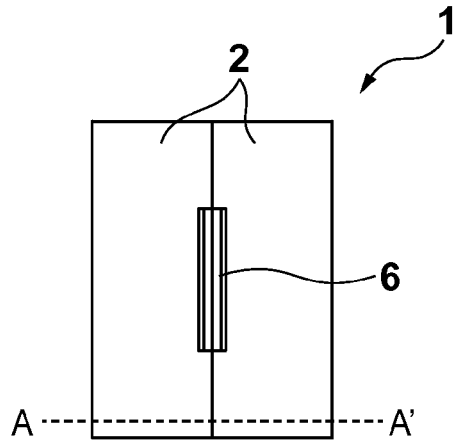
Figure 1C:
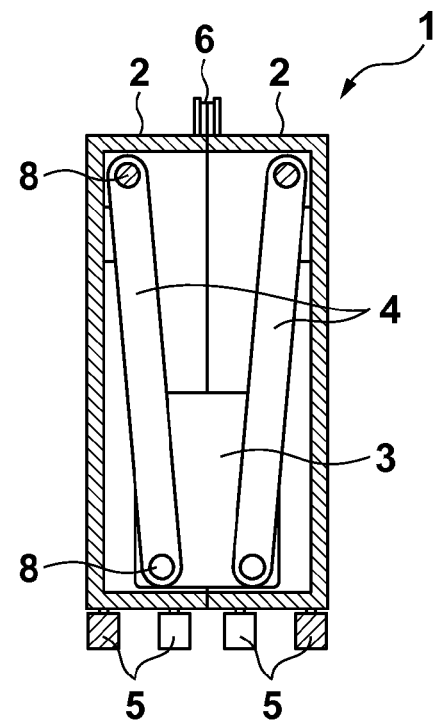

The schematic arrangement of an X-ray imaging apparatus according to the first embodiment at the time of accommodation, transformation, and imaging will be described with reference to FIGS. 1A to 3D. FIGS. 1A to 1C show the schematic arrangement of the X-ray imaging apparatus upon accommodation. FIG. 1A is a perspective view, FIG. 1B is a plan view, and FIG. 1C is a sectional view taken along a line A-A' in the plan view. FIGS. 2A to 2C show the schematic arrangement of the X-ray imaging apparatus upon transformation. FIG. 2A is a perspective view, FIG. 2B is a plan view, and FIG. 2C is a sectional view taken along a line B-B' in the plan view. FIGS. 3A to 3D show the schematic arrangement of the X-ray imaging apparatus upon imaging. FIG. 3A is a perspective view, FIG. 3B is a plan view, FIG. 3C is a sectional view taken along a line C-C' in the plan view, and FIG. 3D is a schematic view showing the use state upon imaging.

An X-ray imaging apparatus 1 includes an accommodation unit 2, an X-ray generation unit 3, and supporting members 4. The accommodation unit 2 can accommodate the X-ray generation unit 3 supported by the supporting members 4 together with the supporting members 4. As shown in FIGS. 1A to 1C, the accommodation unit 2 is formed from two parts (a first member and a second member) so as to have a structure capable of internally accommodating the X-ray generation unit 3 by joining the two parts at the time of accommodation. The accommodation unit 2 functions as an outer case that protects the X-ray generation unit 3 from impact and contamination such as dust. The accommodation unit 2 has handles 6 on the top, which can be used as grips when transporting or extending the apparatus. The accommodation unit 2 also has pulling handles 7 on side surfaces, which can be used as finger hooks when extending the accommodation unit 2. Each pulling handle 7 includes a latch mechanism (not shown). When the user draws the latch actuating plate of the pulling handle 7, the lock is undone to make the accommodation unit 2 extendable. The accommodation unit 2 also includes casters 5 on the bottom and can easily be moved when transporting or transforming the apparatus. To improve the stability when extended, the casters 5 may be provided not only at the four corners but also near the center of the bottom of the accommodation unit 2.

As shown in FIGS. 2A to 2C, when the accommodation unit 2 is extended, and the parts that form the accommodation unit 2 move away in directions to increase the distance between them, the X-ray imaging apparatus transforms to the form for imaging as shown in FIGS. 3A to 3D. The support height of the X-ray generation unit 3 can be adjusted by the distance between the parts. Upon imaging, the accommodation unit 2 functions as part of the frame that holds the X-ray generation unit 3 at an imaging position. For this purpose, the accommodation unit 2 is made of a material having an appropriate strength for the outer case and the frame. The accommodation unit 2 is made of, for example, a plastic such as polycarbonate, a metal, or a combination thereof. X-ray shield members such as lead or tungsten sheets can be provided on the inner or outer surfaces of the accommodation unit 2 to shield X-rays that are emitted by the X-ray generation unit 3 toward the accommodation unit 2 provided with the X-ray shield members upon X-ray imaging. The accommodation unit 2 can also have a space to accommodate other units (not shown) necessary for X-ray imaging, including an X-ray detection sensor, a control unit such as a PC, and a power cable or battery (none are shown) so that the units necessary for X-ray imaging can be transported as a whole.

The X-ray generation unit 3 generates X-rays for medical diagnosis and irradiates a subject S with them. The X-ray generation unit 3 generally uses, for example, an X-ray tube that irradiates an X-ray target made of a bulk metal with thermoelectrons emitted by a filament heated to a high temperature so as to generate X-rays on the electron beam incident side. In this embodiment, as shown in FIG. 3D, the X-ray generation unit 3 is arranged to be located vertically above the imaging part of the subject S, and from that position, irradiates the subject S with X-rays. The X-rays that have passed through the subject S are detected by an X-ray detection sensor (not shown) placed under the subject S, and output as an electrical signal. This output signal undergoes image processing to obtain a so-called X-ray image.

The supporting members 4 have a function of fixing the X-ray generation unit 3 inside the accommodation unit 2 at the time of accommodation and holding the X-ray generation unit 3 at a position suitable for imaging at the time of imaging. In this embodiment, the X-ray generation unit 3 and the accommodation unit 2 are connected by the four supporting members 4, as shown in FIGS. 1A to 3D. One end of each supporting member 4 is rotatably connected by an upper connecting portion (first connecting portion) of the accommodation unit 2. The other end of the supporting member 4 is rotatably connected to the X-ray generation unit 3 by another connecting portion (second connecting portion). Each rotatable connecting portion 8 may include a rotation direction control mechanism for unidirectionally controlling the rotation direction. As the rotation direction control mechanism, a ratchet mechanism is known by those skilled in the art as an implementable technique, and is applicable to the X-ray imaging apparatus 1. When transforming from the form for accommodation to the form for imaging, the rotation directions of the connecting portions of the accommodation unit 2 are controlled such that they can freely rotate in directions in which the parts of the accommodation unit 2 move away from each other but are locked in directions in which the parts move close to each other. The rotation directions of the connecting portions 8 of the X-ray generation unit 3 are controlled such that they can freely rotate in directions in which the X-ray generation unit 3 moves upward but are locked in directions in which the X-ray generation unit 3 moves downward. The rotation direction control mechanism can switch the rotation direction to be controlled. When transforming from the form for imaging to the form for accommodation, the rotation direction control mechanism can control to act reversely. More specifically, the rotation directions of the connecting portions 8 of the accommodation unit 2 are controlled such that they can freely rotate in directions in which the parts of the accommodation unit 2 move close to each other but are locked in directions in which the parts move away from each other. The rotation directions of the connecting portions 8 of the X-ray generation unit 3 are controlled such that they can freely rotate in directions in which the X-ray generation unit 3 moves downward but are locked in directions in which the X-ray generation unit 3 moves upward. When at least one of the connecting portions 8 is provided with the rotation direction control mechanism to control the rotation direction, any accident caused by downward movement of the X-ray generation unit 3 due to its own weight and the resultant closing in of the accommodation unit 2 can be prevented.

With the above-described arrangement, when the parts of the accommodation unit 2 move away to increase the distance between them, the X-ray generation unit 3 moves upward along with the change of the supporting members 4 from the substantially vertical state to the substantially horizontal state, and the X-ray imaging apparatus transforms to the state for imaging, as shown in FIGS. 1A to 3D. When the X-ray imaging has ended, the X-ray generation unit 3 is accommodated in the accommodation unit 2 in accordance with a reverse procedure. More specifically, when the plurality of parts of the accommodation unit 2 move close to each other, the X-ray generation unit 3 moves downward along with the change of the supporting members 4 from the substantially horizontal state to the substantially vertical state and is accommodated in the accommodation unit 2.

As described above, according to this embodiment, since the accommodation unit, the X-ray generation unit, and the supporting members are integrated, it is possible to improve the portability and prevent an accident caused by drop of a part upon extension or accommodation. It is also possible to install and accommodate the X-ray generation unit by a simple operation of increasing or decreasing the interval between the parts of the accommodation unit and decrease the labor and time.

Second Embodiment

An X-ray imaging apparatus 1 according to the second embodiment is configured to be able to extend/contract an accommodation unit 2 or supporting members 4 functioning as a frame for holding an X-ray generation unit 3 at the time of imaging to enable X-ray imaging under various imaging conditions.

Figure 4A:
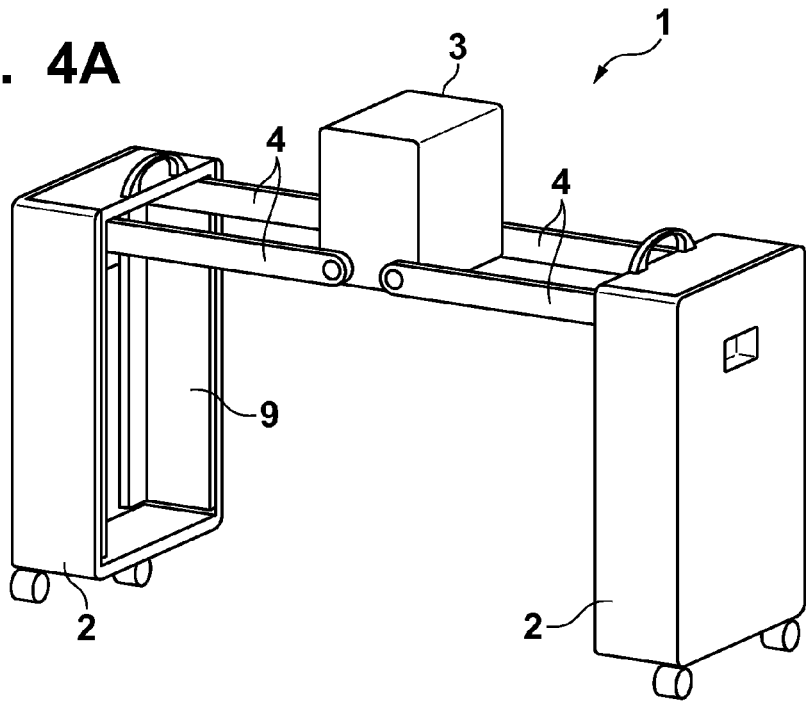
FIGS. 4A and 4B are perspective views showing the schematic arrangement of an X-ray imaging apparatus according to the second embodiment.
Figure 4B:
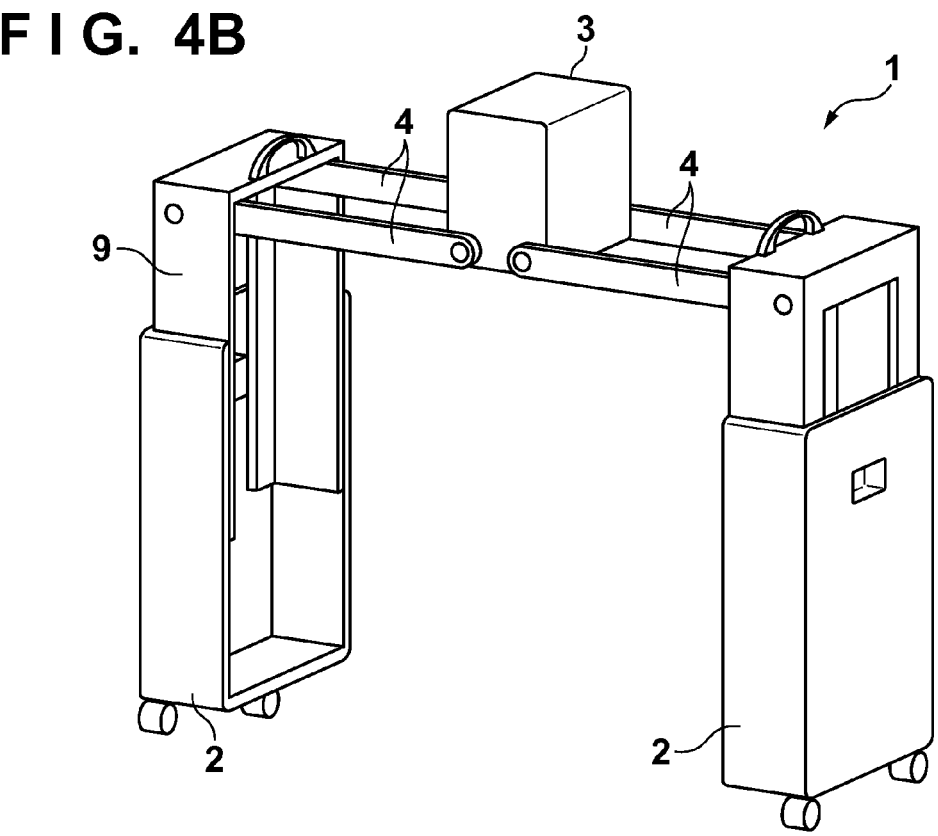

An X-ray imaging apparatus capable of extending/contracting the accommodation unit 2 will be described first with reference to FIGS. 4A and 4B. As shown in FIG. 4A, each part of the accommodation unit 2 can extend/contract. More specifically, stretching portions 9 included in the accommodation unit 2 slide in the vertical direction inside the accommodation unit 2, thereby changing the height to hold the X-ray generation unit 3. This allows performance of X-ray imaging of subjects S lying down at various heights on a floor surface, a bed surface, or the like.

An X-ray imaging apparatus capable of extending/contracting the supporting members 4 will be described next with reference to FIG. 5. As shown in FIG. 5, the plurality of supporting members 4 can extend/contract. More specifically, stretching portions 10 included in the supporting members 4 slide inside or along the inner surfaces of the supporting members 4, thereby further increasing the interval between the parts of the accommodation unit 2. This allows performance of X-ray imaging on, for example, a bed wider than the standard.

It is also possible to employ both the extend/contract structure of the accommodation unit 2 and stretch/contract structure of the supporting members 4 to enable X-ray imaging in correspondence with various heights and widths. In addition, the X-ray imaging apparatus 1 can be moved to the position of the subject S after extending while avoiding a tall or wide obstacle.

Third Embodiment

In an X-ray imaging apparatus 1 according to the third embodiment, the X-ray generation unit can be made into a thin planar shape and arranged between the supporting members. The thin planar X-ray generation unit is formed from an X-ray source that generally uses a cold-cathode multi-electron source. In the X-ray source using the multi-electron source, the respective electron sources are made small and arranged in an array. Hence, a flat thin X-ray source can be implemented.

Figure 6A:
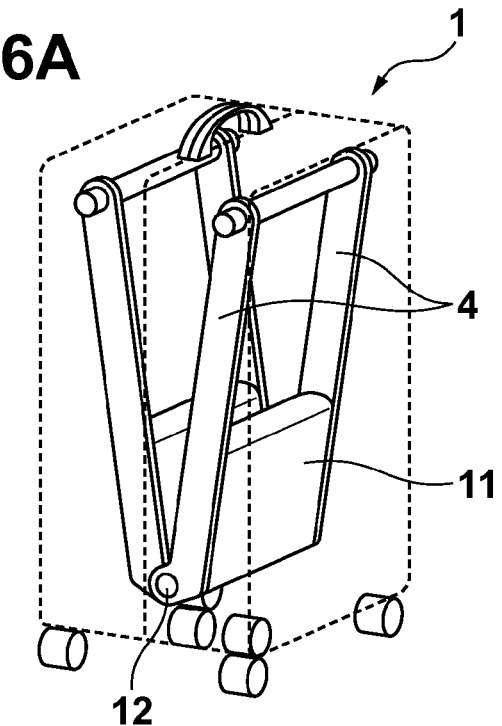
FIGS. 6A and 6B are perspective views showing the schematic arrangement of an X-ray imaging apparatus according to the third embodiment.
Figure 6B:
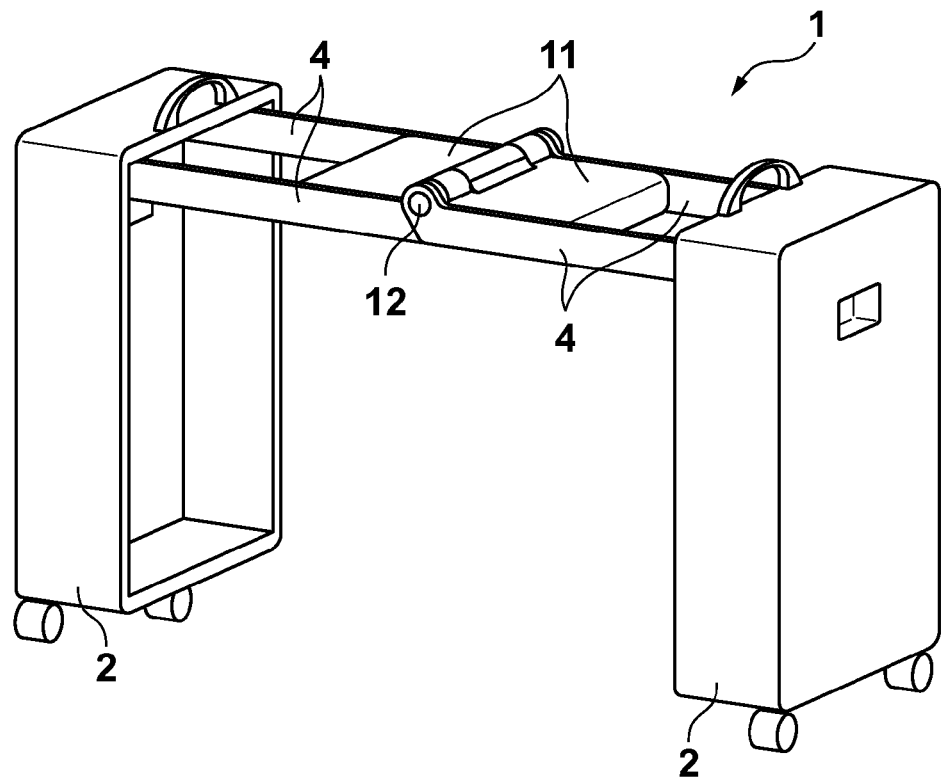

The X-ray imaging apparatus according to the third embodiment will be described with reference to FIGS. 6A and 6B. FIG. 6A is a perspective view of a state upon accommodation, and FIG. 6B is a perspective view of a state upon imaging. Note that in FIG. 6A, the accommodation unit 2 is indicated by broken lines to show the internal structure.

A planar X-ray generation unit 11 designated to have almost the same thickness as that of supporting members 4 is arranged to be symmetrical about a rotation axis 12 between supporting members 4. The planar X-ray generation unit 11 is folded at the time of accommodation shown in FIG. 6A. Upon imaging shown in FIG. 6B, the planar X-ray generation unit 11 can transform to a flat shape and uniformly irradiate a subject S with X-rays.

As described above, the X-ray imaging apparatus according to this embodiment can be compact as a whole at the time of accommodation because it has no members projecting on the upper and lower sides of the supporting members. In addition, when moving the X-ray imaging apparatus to the position of the subject after extended, accidents such as collision of the X-ray generation unit with an obstacle can be reduced. Furthermore, since the fixing portions between the supporting members and the X-ray generation unit are linear, and the load of the X-ray generation unit on the supporting members is divided, the X-ray imaging apparatus can be extended or accommodated by a smaller force.

According to the present invention, it is possible to provide an X-ray imaging apparatus that is convenient in transport and installation and can perform X-ray imaging in correspondence with various imaging conditions.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-009430 filed on Jan. 19, 2012, which is hereby incorporated by reference herein in its entirety.

What is claimed is:

1. An X-ray imaging apparatus comprising:
an X-ray generation unit;
a plurality of supporting members configured to support said X-ray generation unit; and
an accommodation unit configured to accommodate said X-ray generation unit and said plurality of supporting members,
wherein said accommodation unit is formed by bringing a first member and a second member into contact with each other,
each of said plurality of supporting members is connected to said first member by a first connecting portion that is rotatable and to said X-ray generation unit by a second connecting portion that is rotatable, and
a support height of said X-ray generation unit supported by said supporting members can be adjusted in accordance with a distance between said first member and said second member.

2. The apparatus according to claim 1, wherein said X-ray generation unit moves upward when said first member and said second member move away from each other to increase the distance, and moves downward when said first member and said second member move close to each other to decrease the distance.

3. The apparatus according to claim 1, further comprising a rotation direction control mechanism configured to unidirectionally control a rotation direction of one of said first connecting portion and said second connecting portion.

4. The apparatus according to claim 1, wherein said accommodation unit can extend/contract in a vertical direction.

5. The apparatus according to claim 1, wherein said plurality of supporting members can stretch/contract along said supporting members.

6. The apparatus according to claim 1, wherein said X-ray generation unit is formed into a planar shape and fitted between said plurality of supporting members.

7. An X-ray imaging apparatus comprising:
an X-ray generation unit;
a plurality of supporting members configured to support said X-ray generation unit; and
an accommodation unit configured to accommodate said X-ray generation unit and said plurality of supporting members,
wherein said accommodation unit is formed by bringing a first member and a second member into contact with each other, and
wherein a first supporting member of said plurality of supporting members is connected to said first member by a first connecting portion that is rotatable, and a second supporting member of said plurality of supporting members is connected to said second member by a second connecting portion that is rotatable.

8. The apparatus according to claim 7, wherein said X-ray generation unit moves upward when said first member and said second member move away from each other to increase the distance, and moves downward when said first member and said second member move close to each other to decrease the distance.

9. The apparatus according to claim 7, further comprising a rotation direction control mechanism configured to unidirectionally control a rotation direction of one of said first connecting portion and said second connecting portion.

10. The apparatus according to claim 7, wherein said accommodation unit can extend/contract in a vertical direction.

11. The apparatus according to claim 7, wherein said plurality of supporting members can stretch/contract along said supporting members.

12. The apparatus according to claim 7, wherein said X-ray generation unit is formed into a planar shape and fitted between said plurality of supporting members.

13. The apparatus according to claim 7, wherein in a case where said first member and said second member that form the accommodation unit move away in directions to increase the distance between said first member and said second member, the X-ray imaging apparatus transforms from the form for accommodation to the form for imaging.

14. The apparatus according to claim 7, wherein in case where the X-ray imaging apparatus transforms from the form for accommodation to the form for imaging, the connecting portions of said accommodation unit rotate in directions in which said first member and said second member of the accommodation unit move away from each other.

15. An X-ray imaging apparatus comprising:
an X-ray generation unit;
a plurality of supporting members configured to support said X-ray generation unit; and
an accommodation unit configured to accommodate said X-ray generation unit and said plurality of supporting members,
wherein said accommodation unit is formed by bringing a first member and a second member into contact with each other,
wherein in a case where said first member and said second member that form the accommodation unit move away in directions to increase the distance between said first member and said second member, the X-ray imaging apparatus transforms from the form for accommodation to the form for imaging.

* * * * *